United States Patent [19]
Misaki et al.

[11] Patent Number: 5,117,467
[45] Date of Patent: May 26, 1992

[54] COLONY COUNTING APPARATUS

[75] Inventors: Hideo Misaki; Shigeru Ueda, both of Shizuoka; Kazuhiro Watanabe; Yuzo Ishikawa, both of Tokyo; Hirao Nagae, Ageo; Takashi Matsuzawa, Kawaguchi, all of Japan

[73] Assignees: Toyo Jozo Co., Ltd., Tagata; Nemoto & Co., Ltd., Suginami, both of Japan

[21] Appl. No.: 714,368

[22] Filed: Jun. 12, 1991

Related U.S. Application Data

[63] Continuation of Ser. No. 354,554, May 22, 1989, abandoned.

[30] Foreign Application Priority Data

May 23, 1988 [JP] Japan .................. 63-125365

[51] Int. Cl.$^5$ .................. G06K 9/00; G06M 7/00; G06M 11/02
[52] U.S. Cl. .................. 382/6; 377/6; 377/10; 382/1
[58] Field of Search .................. 382/6, 1, 34; 377/6, 377/10

[56] References Cited

U.S. PATENT DOCUMENTS

| | | | |
|---|---|---|---|
| 2,803,406 | 8/1957 | Nuttall | 382/6 |
| 3,811,036 | 5/1974 | Perry | 377/10 |
| 3,867,613 | 2/1975 | Schoon | 377/10 |

Primary Examiner—Leo H. Boudreau
Assistant Examiner—Michael Cammarata
Attorney, Agent, or Firm—Armstrong, Nikaido, Marmelstein, Kubovcik & Murray

[57] ABSTRACT

A colony counting apparatus includes a reading unit with a visual sensor incorporated therein. The presence of a colony is detected at the end of that colony by moving the reading unit along lines selected at an appropriate pitch and by reading data on the individual points set along each line as logical high or low signals. The values obtained in the above-described counting operation are added and stored in an addition/storage device in a CPU, and the results of addition which are stored in the addition/storage device are output to a suitable display by an outputting device when the counting operation is completed.

2 Claims, 7 Drawing Sheets

COLONY COUNTING APPARATUS

This application is a continuation of application Ser. No. 354,554 filed May 22, 1989 now abandoned.

BACKGROUND OF THE INVENTION

1. Field of the Invention

The present invention relates to a colony counting apparatus, and more particularly, to a colony counting apparatus for counting numbers of colonies with a visual sensor.

2. Description of the Related Art

Apparati for counting numbers of colonies are already known.

In such conventional colony counting apparatuses, a Schale in which colonies of bacteria are grown is divided into a plurality of areas on which a colony number—reading operation is performed by a reading unit, and the number of colonies of bacteria growing in the Schale is counted by counting the numbers of colonies located in the individual areas.

In the above-described colony counting apparatus, each of the areas on which a colony counting operation is performed is scanned by moving the reading unit along scanning lines that run in one direction. When the reading unit completes scanning along one scanning line, it is moved in the direction perpendicular to the scanning direction and then scans the subsequent scanning line. Each time the reading unit is moved along one scanning line, the number of colonies recognized on that scanning line is stored. The numbers of colonies counted in the individual areas are added to obtain the number of colonies in the overall areas in the Schale.

In the conventional colony counting apparatus, the circle of each colony is recognized using a plurality of scanning lines, one colony being detected when one colony circle is recognized. In consequence, the overall shape of the circle must be read to recognize one colony, requiring a very large capacity storage unit.

SUMMARY OF THE INVENTION

Accordingly, an object of the present invention is to provide a colony counting apparatus in which a colony can be detected by running a reading unit along scanning lines and by comparing the data which is read with the stored data on the points located between the corresponding point on a previous scanning line and the previous point on the present line, so that a small capacity storage unit will suffice, thereby allowing the apparatus to be made compact.

To this end, the present invention provides a colony counting apparatus which includes, a reading unit with a visual sensor incorporated therein. The visual sensor reads the data on individual points located on a line as logical high or low signals. A point storage device stores the results of reading performed by the reading unit until reading is performed on a subsequent point on a subsequent line. A point comparison device compares the data on the previous point and the present point on the present line which is being read at present with the data on the previous point and the present point on the previous line stored in the point storage device. A rewriting device erases the data on the previous point on the previous line after the comparison has been performed by the comparison device and stores the data on the present point on the present line in the point storage device. An addition/storage device adds and stores a value by the counting output from the comparison device. and An output device outputs the results of the addition performed by the addition/storage device. The comparison device outputs an addition output in correspondence with a change in the previous data from the logical high level to the logical low level, which occurs when the present data is at the logical low level while the previous data is at the logical low, high, and then low levels.

In the present invention, when the number of colonies is to be counted, the presence of a colony is detected at the terminating end of that colony confirmed using scanning lines.

More specifically, in the present invention, lines are provided in a predetermined direction with respect to the colonies, and data is read at individual points provided along each line as logical high or low signals by the visual sensor. The results of the reading performed at the individual points are stored in the storage device. A number of colonies is counted by comparing the data on a certain portion on the present line which is being read with the stored data on the points located between the previous point of the corresponding portion on a previous line and the previous point on the present line.

In consequence, since only the data on the points located from the previous point on the previous line to the previous point on the present line, i.e., the data corresponding to 1 line, should be stored in the storage device, the overall storage capacity can be reduced extremely, making the reduction in the overall size of the apparatus possible.

DETAILED DESCRIPTION OF THE PREFERRED EMBODIMENTS

A first embodiment of the present invention will now be described below with reference to the accompanying drawings.

Figure 1:
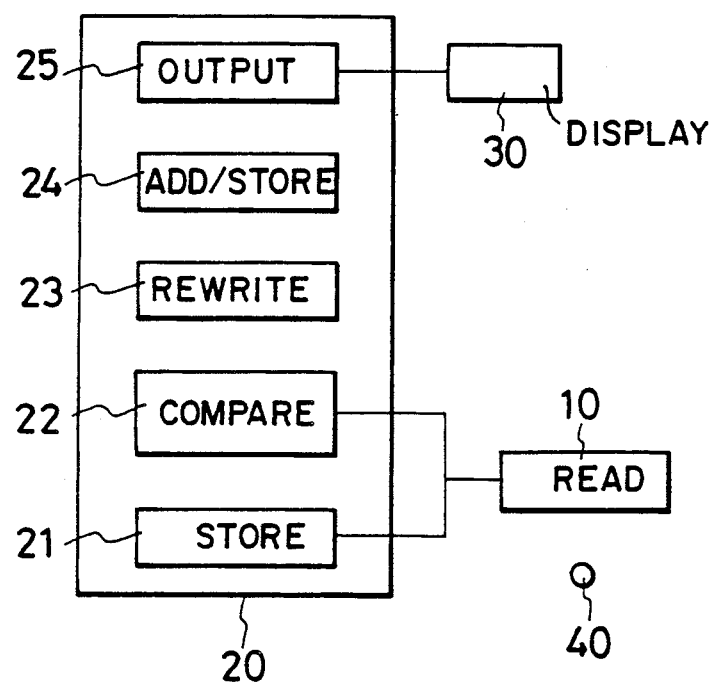
FIG. 1 is a block diagram of a colony counting apparatus according to the present invention.

Referring first to FIG. 1, a colony counting apparatus according to the present invention includes: a reading unit 10 for reading the presence of colonies 40; and a CPU 20 having a storage means 21 for storing the results of the reading performed by the reading unit 10, a comparison means 22 for comparing the data on the previous point and the present point located on a previous line with the data on the previous point and the present point located on the present line, an addition/storage means 24 for adding and storing the colony value confirmed by the comparison means 22, and an output means 25 for outputting the contents of the addition/storage means 24 to a display 30. The CPU 20 further includes a rewriting means 23 for sequentially rewriting the data on the previous line which is stored in the storage means 21 with the data read by the reading unit 10.

Figure 2:
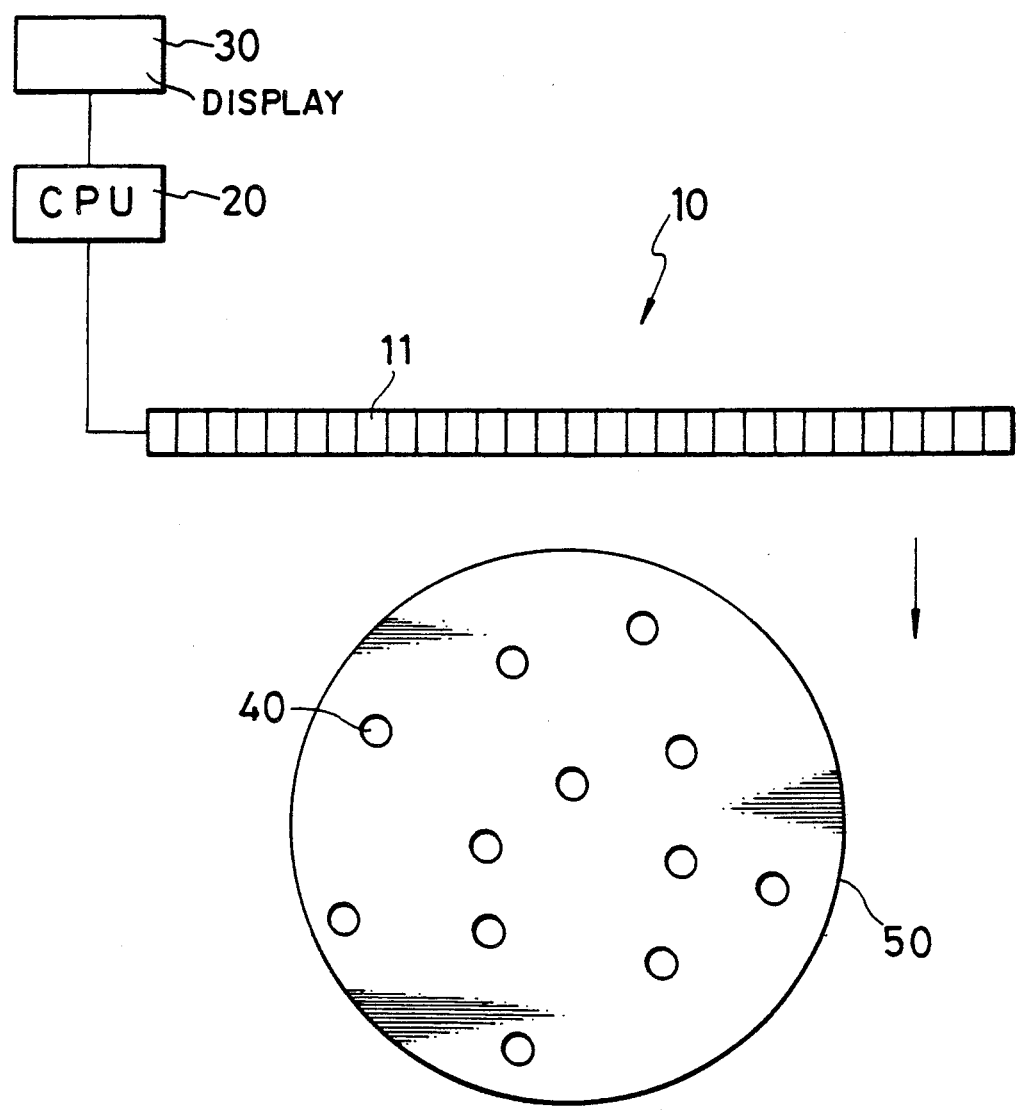
FIG. 2 is a schematic view of the colony counting apparatus of FIG. 1.

As shown in FIG. 2, the number of colonies 40 of bacteria growing in a circular Schale 50 is counted by the CPU 20 by running the reading unit 10 with a large number of visual sensors 11 incorporated therein for scanning purposes at a predetermined pitch. The number of colonies 40 counted is displayed on the display 30.

For the convenience of illustration, the reading unit 10 shown in FIG. 2 incorporates a large number of visual sensors 11. However, a single visual sensor 11 may also be incorporated in the reading unit 10. In that case, colonies 40 may be detected by moving the single visual sensor 11 in the longitudinal direction of the reading unit 10 for scanning.

Figure 3:
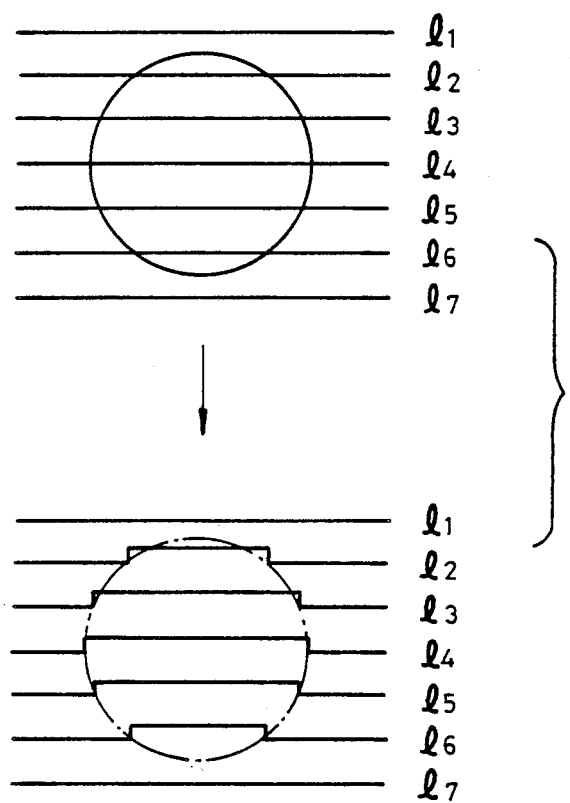
FIG. 3 illustrates how a single colony is detected as logical high and low signals by the colony counting apparatus according to the present invention.

In the colony counting apparatus according to the present invention, a colony 40 is detected by detecting the starting end and the terminating end of a substantially circular colony on each scanning line with the visual sensors 11 of the reading unit 10, as shown in FIG. 3.

FIG. 3 shows a single colony 40 located between line 1 and line 7. In this case, only logical low signals are output on the lines 1 and 7. On each of the lines 2 to 6, the starting point and the terminating end of the colony 40 are recognized by the output of first a logical low signal, next a logical high signal, and then a logical low signal again.

In an actual operation, a plurality of points are provided on each of the lines, and the colony 40 is detected by the visual sensors 11 at the individual points along each line. From line 2 to line 3 shown in FIG. 6, the visual sensors 11 detect a colony 40 by outputting logical high and low signals.

A procedure for detecting the presence or absence of a colony 40 will be described below with reference to the flowchart in FIG. 4. In this colony detection technique, detection of the presence or absence of a colony 40 is made at individual points set along the two scanning lines, which are referred to as the previous line and the present line.

Figure 5:
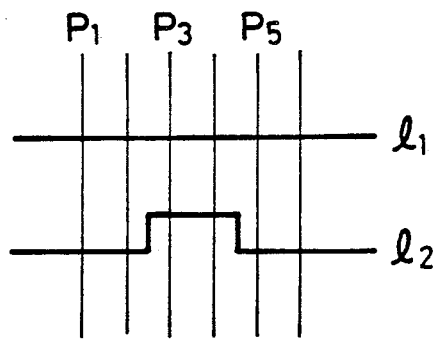
FIGS. 5 to 12 illustrates examples of the relationship between a previous line and a present line, which can be considered in colony counting.

FIG. 5 illustrates a starting portion of the colony 40 shown in FIG. 3.

When the portion of the colony 40 is in a state indicated by the relationship between line 1 and line 2 shown in FIG. 5, there is a possibility that reading of the reading device 10 has just started. In consequence, as the answer to the determination to be made in step 1 in the flowchart shown in FIG. 4, both the case in which counting is permitted and that in which it is not permitted can be considered.

A case in which counting is not permitted is considered first.

In the detection made at point 1 in the state shown in FIG. 5, the data stored in the memory and the present data are all at the logical low level.

Figure 4:
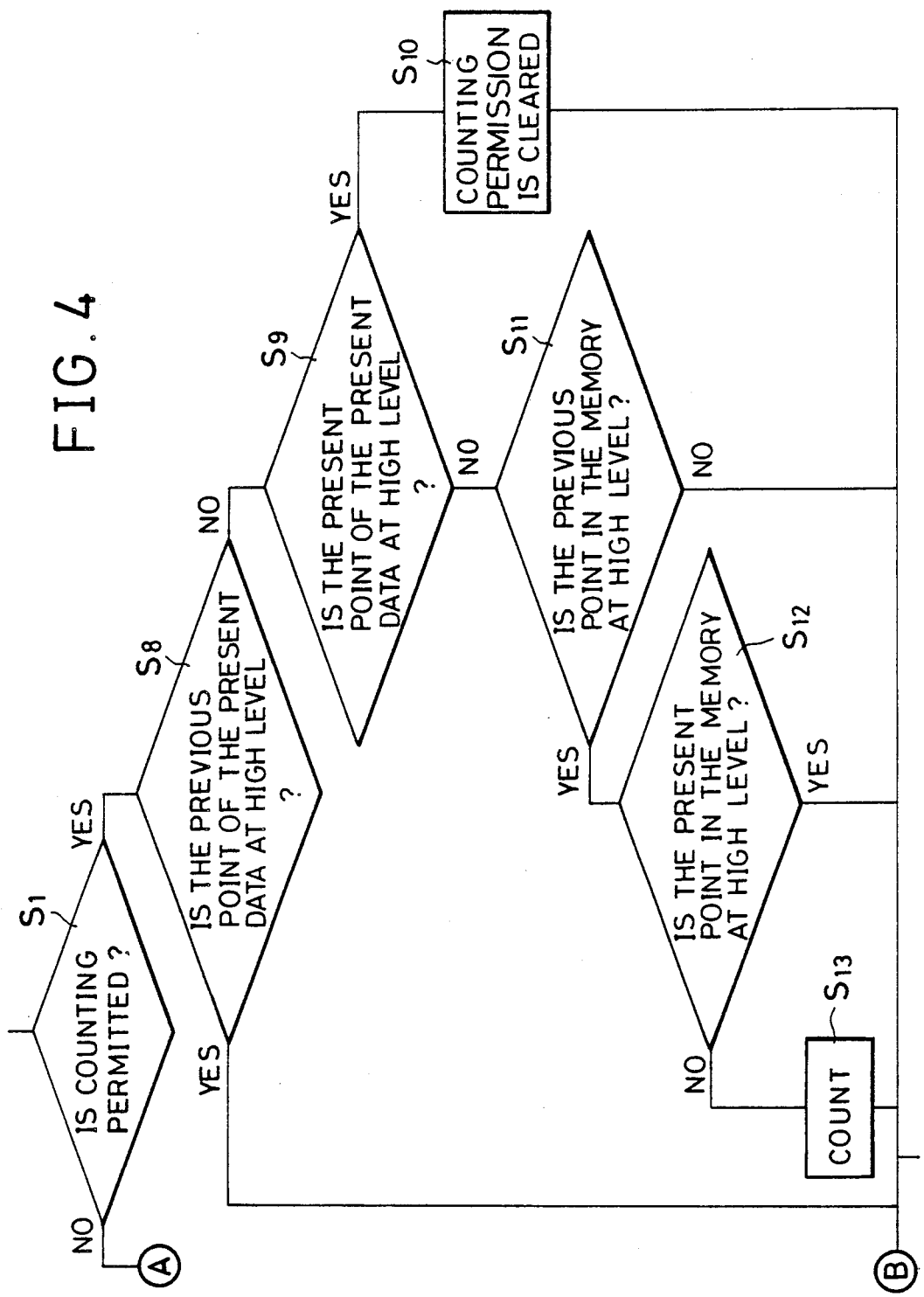
FIG. 4 is a flowchart of the control operation performed by a point storage means and a point comparison means in a CPU.

A detection is made at point 2 in accordance with the control routine shown in the flowchart in FIG. 4. As the answer to the determination made in step 1 as to whether or not counting is permitted, it is now assumed that the counting is not permitted, and the processing then goes to step 2.

In step 2, it is determined whether or not the previous point in the memory is at the logical high level. Since point 1 which is the previous point in the memory is at the logical low level, the processing goes to step 3.

In step 3, it is determined whether or not the previous point of the present data is at the logical high state. However, point 1 on the line 2 which is the previous point of the present data is at the logical low level, so the detection made at point 2 is completed at this determination, and a detection then goes to that at point 3.

In the detection made at point 3, since both the previous point in the memory and the previous point of the present data are at the logical low level, processings in steps 1, 2 and 3 are sequentially executed, as in the detection at point 2, thereby completing the detection made at point 3.

A detection is made at point 4. In this detection, since the previous point in the memory is at the logical low level, the processings in the steps 1 and 2 are successively executed, and the process then goes to step 3 where it is determined whether or not the previous point of the present data is at the logical high level. Since the point 3 on the line 2 which is the previous point of the present data is at the logical high level, the processing proceeds to step 4 in which it is determined whether or not the present point of the present data is at the logical high level. However, the present point of the present data is at the logical high level at point 4, so the detection made at the point 4 is completed at the determination made in step 4. Next, a detection is made at point 5.

In this detection, the processings in steps 1, 2, 3 and are successively executed, as in the detection made at the point 4. However, in the determination made in step 4, since the present point of the present data is at the logical low level, the processing proceeds to step 5 in which counting permission is given for the first time.

In consequence, even if the detection on the state shown in FIG. 5 is started under the condition that counting is not permitted, counting permission condition is given in a state where no counting is done when the detection at the point 5 is completed.

Further, in the detection made on the state shown in FIG. 5, a case in which detection is started under the condition that counting is permitted will be described below.

In this case, the processing proceeds from step 1 to step 8 in which it is determined whether or not the previous point of the present data is at the logical high level. When this determination is made on the point 2, since the previous point of the present data is at the logical low level, the processing goes from step 8 to step 9.

In step 9, it is determined whether or not the present point of the present data is at the logical high level. Since the present point of the present data is at the logical low level, the processing goes to step 11.

In step 11, it is determined whether or not the previous point in the memory is at the logical high level. Since the previous point in the memory is at the logical low level, the detection made at point 2 is completed at this determination, and a detection proceeds to that at point 3.

In the detection made at the point 3, since the processing of step 10 in which counting permission is cleared has not yet been executed, the counting permission condition is held, and the processing proceeds from step 1 to step 8.

In the determination made in step 8, since the previous point of the present data is at the logical low level at point 3, the processing goes to step 9.

In the determination made in step 9, since the present point of the present data is at the logical high level, the processing proceeds to step 10 in which counting permission is cleared. In consequence, in the detections to be made at the point 4 and the subsequent points, detection is started under the condition that counting is not permitted, i.e., the processing goes from step 1 to step 2.

Thus, in the case of the state shown in FIG. 5, whether a detection is made at the point 1 or point 2 under the condition that counting permission is given or not given, it is determined in the detection made at the point 3 that counting permission is not given. Thereafter, in the detection made at the point 5, counting permission is given. In consequence, under whatever condition the detection on the state shown in FIG. 5 is started, counting is permitted by the time the processing indicated by the flowchart in FIG. 4 has been completed. Further, the processing is completed in a state where no counting is done.

Figure 6:
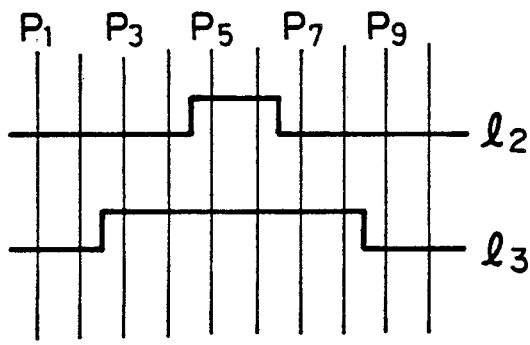

A state shown in FIG. 6 represents a relationship between the line 2 and the line 3 in the figure shown in FIG. 3, i.e, a relationship between a line on which the detection of a colony 40 is started and a subsequent line.

The state shown in FIG. 6 represents either a case in which the relationship shown in FIG. 5 has been detected previously or a case in which the state shown in FIG. 6 is directly detected, that is, in which a colony 40 is attaching, for example, to the wall of the Schale 50.

Thus, in the detection made on the state shown in FIG. 6, a detection is started under both condition that counting is permitted and that counting is not permitted.

In this state shown in FIG. 6, it is to be noted that detections are made at the points 1 to 4 in the same way as that in which detections are made at the points 1 to 4 in the state shown in FIG. 5, description thereof being omitted.

As has been stated in the description made on the state shown in FIG. 5, even if the detection is started under the condition that counting is permitted, counting permission is cleared in the processing of step 10 when a detection is completed at the point 3.

Hence, in the detection to be made on the state shown in FIG. 6, a detection is started at the point 4 and the subsequent points under the condition that counting is not permitted.

Since the counting is not permitted when the detection is started at the point 4, the processing goes from step 1 to step 2. In the determination made in step 2, since the previous point in the memory is not at the logical high level, the processing goes to step 3. However, both the previous point and the present point of the present data are at the logical high level, so the detection made at the point 4 is completed after the processing in step 4 has been executed. Next, a detection is made at the point 5.

In the detection made at the point 5, since the previous point in the memory is at the logical low level while the previous point and the present point of the present data are at the logical high level, the processing in steps 1, 2, 3 and 4 are sequentially executed as in the detection made at point 4, and a detection then proceeds to that at point 6.

In the detection made at point 6, the previous point in the memory is at the logical high level, so the processings in steps 1, 2 and 6 are sequentially executed. However, since the present point in the memory is at the logical high level, the detection at the point 6 is completed at the determination made in step 6.

In the detection made at point 7, since the previous point in the memory is at the logical high level while the present point in the memory is at the logical low level, processing proceeds from step 6 to step 7 in which counting is permitted, thereby completing the detection at point 7.

Thus, counting is permitted after the detection at the point 7 has been completed.

Next, a detection is made at point 8. This detection is started under the condition that counting is permitted. However, since the previous point of the present data is at the logical high level, the detection at the point 8 is completed at the determination made in step 8, and a detection proceeds to that at point 9.

In the detection made at point 9, since the previous point of the present data is at the logical high level as in the detection made at point 8, the detection is completed at the determination made in step 8. Next, a detection is made at point 10.

At point 10, the previous point of the present data, the present point of the present data and the previous point in the memory are all at the logical low level. The detection is therefore completed at point 10 after the processings of steps 8, 9 and 11 have been sequentially executed.

Thus, in the state shown in FIG. 6, no counting is done. However, the detection on the state shown in FIG. 6 is completed in a state that counting is permitted.

Next, a state shown in FIG. 7 will be described. Since the state shown in FIG. 7 also represents a case in which a colony 40 is attaching to the wall of the Schale 50, detection is made on the state shown in FIG. 7 under both condition that counting is permitted and is not permitted.

First, a case in which counting is not permitted will be described.

At point 2, the previous point in the memory and the previous point of the present data are at the logical low level. In consequence, the detection at the point 2 is completed after the processings in Steps 1, 2 and 3 have been sequentially executed.

At point 3, the previous point in the memory and the previous point of the present point are at the logical low level. In consequence, the detection at the point 3 is completed after the processings in steps 1, 2 and 3 have been sequentially executed, as in the detection made on the point 2.

In the detection made at point 4, since the previous point in the memory and the present point in the memory are both at the logical high level, the processing proceeds from step 2 to step 6, thereby completing the detection at the point 4.

In the detection made at point 5, since the previous point in the memory and the present point in the memory are both at the logical high level, as in the detection made at point 4, the processing proceeds from step 2 to step 6, thereby completing the detection at the point 5.

Figure 7:
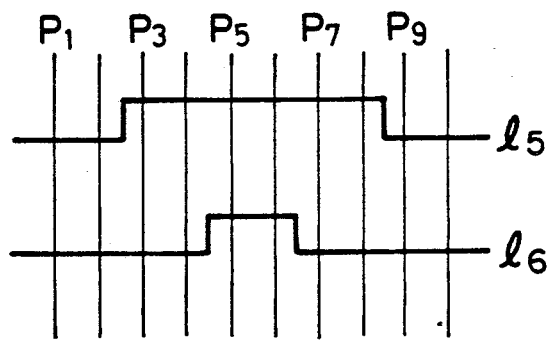

In a case where the detection on the state shown in FIG. 7 is started under the condition that counting is permitted, at point 2, the previous point of the present data, the present point of the present data and the previous point in the memory are all at the logical low level. As a result, the processings in steps 1, 8, 9 and 11 are sequentially executed, thereby completing the detection at the point 2.

In the detection at point 3, since the previous point of the present data, the present point of the present data and the previous point in the memory are all at the logical low level, as in the detection at the point 2. As a result, the processings in steps 1, 8, 9 and 11 are sequentially executed, thereby completing the detection at point 3.

At point 4, the previous point and the present point of the present data are both at the logical low level, whereas the previous point in the memory is at the logical high level. In consequence, the processing flows from step 1, step 8, step 9, step 11 and then step 12. However, since the present point in the memory is at the logical high level, the detection at the point 4 is completed at the determination made in step 12, and the detection proceeds to that at point 5.

At point 5, the previous point of the present data is at the logical low level, whereas the present point of the present data is at the logical high level. In consequence, the processing flows from step 1, step 8, step 9 and then step 10, and counting permission is thereby cleared in step 10. Next, a detection is made at point 6.

Thus, in the pattern shown in FIG. 7, whether the detection is started at point 1 under the condition that permission is permitted or is not permitted, counting permission is cleared when the detection is completed at point 5.

Next, a detection to be made at point 6 will be described. As stated above, the detection at point 6 is started under the condition that counting is not permitted.

In this state in which counting is not permitted, since the previous point in the memory and the present point in the memory are both at the logical high level at points 6, 7 and 8, the processing goes from step 2 to step 6 in the detection made at points 6, 7 and 8.

In the detection made at point 9, since the previous point in the memory is at the logical high level while the present point in the memory is at the logical low level, the processings in steps 1, 2, 6 and 7 are sequentially executed, and counting is thereby permitted in step 7. A detection then proceeds to that at point 10.

Thus, in the pattern shown in FIG. 7, whether detection is started under the condition that counting is permitted or not permitted, counting is permitted in a state where no counting is done when the detection on the pattern shown in FIG. 7 is completed.

Next, a state shown in FIG. 8 will be described. This state represents a state where the data in the memory is at the logical high level for a very short period of time whereas the present data corresponding to that in the memory is all at the logical low level. In other words, this state represents a relationship between the line 6 and the line 7 shown in FIG. 2, i.e., the terminating end of a colony 40.

Figure 8:
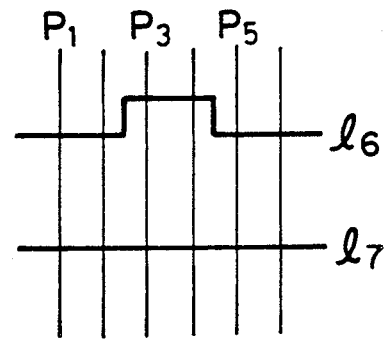

Further, the state shown in FIG. 8 cannot be considered as a state in which a colony 40 is attaching to, for example, the wall of the Schale 50. It is therefore considered as a state which is detected after the detection on the pattern shown in any of FIGS. 5, 6 and 7 has been completed.

The detection on the state shown in any of FIGS. 5, 6 and 7 is completed in a state where counting is permitted. In consequence, in the detection made on the state shown in FIG. 8, counting is already permitted when the detection is started at point 1. A case in which counting is permitted will therefore be described below.

In the state shown in FIG. 8, the previous point of the present data, the present point of the present data and the previous point in the memory are all at the logical low level at points 2 and 3. In consequence, the processings in steps 1, 8, 9 and 11 are sequentially executed in the detection made at points 2 and 3.

At point 4, the previous point of the present data and the present point of the present data are at the logical low level whereas the previous point in the memory is at the logical high level. In consequence, in the detection made at point 4, the processings in steps 1, 8, 9 and 11 are sequentially executed, and the processing then goes to step 12. However, since the present point in the memory is at the logical high level, the detection at the point 4 is completed at the determination made in step 12, and the detection proceeds to that at point 5.

At point 5, the previous point and the present point of the present data are both at the logical low level. In consequence, in the detection made at point 5, the processings in steps 1, 8, 9 and 11 are sequentially executed. Further, since the previous point in the memory is at the logical high level while the present point in the memory is at the logical low level, the processing goes from step 12 to step 13 where counting is performed.

In other words, when the detection at point 5 is completed, the presence of one colony 40 is counted. Even after counting of one colony has been conducted, counting is still permitted because the processing in step 10 in which counting permission is cleared is not yet executed.

Next, a state shown in FIG. 9 will be described. This state represents a state in which the terminating end of a colony 40 and the starting of another colony 40 are present relatively adjacent to each other.

In this case, since the detection made at points 1 to 5 are the same as that made on the state shown in FIG. 8, a detection is started at points 6 to 9 in a state wherein one colony has been counted and wherein counting is permitted.

However, the detection made at points 6 to 9 are the same as that made on the pattern shown in FIG. 5. That is, in the detection made at point 7, counting permission is cleared, and counting is permitted in the detection made at point 9.

Figure 9:
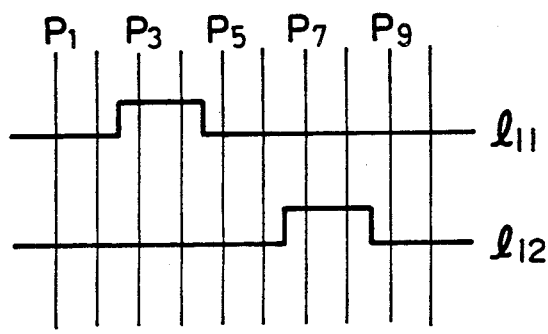

Thus, in the state shown in FIG. 9, counting is performed in the detection made at point 5, and counting is permitted in the detection made at point 9. In consequence, in the detection made on the state shown in FIG. 8, the number of colonies is increased by one, and the detection is completed in a state where counting is permitted.

Figure 10:
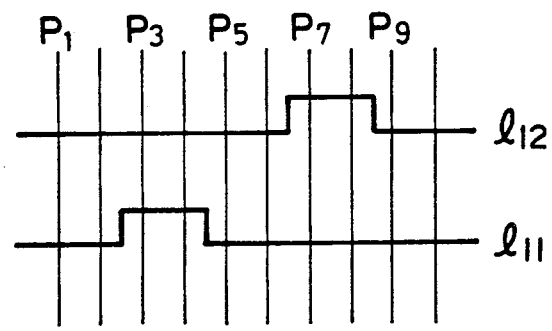

A state shown in FIG. 10 represents a state in which the line 11 and the line 12 in FIG. 9 are exchanged with each In the detection made on this state shown in FIG. 10, counting is permitted when the detection at point 5 is completed, as in the detection made on the state shown in FIG. 5, but no counting is done.

Further, the detection made at points 6 to 9 are the same as that made on the state shown in FIG. 8. That is, counting is done in the detection made at point 9, and the detection on the state shown in FIG. 10 is completed in a state where counting is permitted.

Thus, in the state shown in FIG. 10, the number of colonies is increased by one, and counting is permitted when the detection made on the state shown in FIG. 10 is completed.

Next, a state shown in FIG. 11 will be described.

Figure 11:
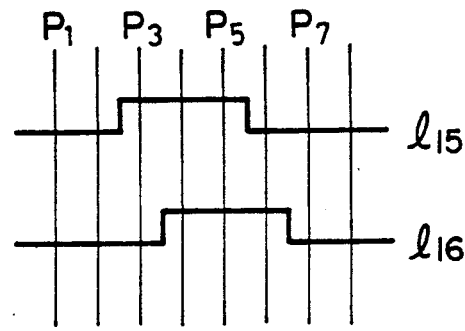

The state shown in FIG. 11 may also represent a state in which a colony is attached to, for example, the wall of the Schale 50. In consequence, both the case in which counting is permitted and that in which it is not permitted can be considered. A case in which counting is not permitted will be described first.

At points 2 and 3, the previous point in the memory and the previous point of the present data are both at the logical low level. In consequence, in the detection made at points 2 and 3, the processings in steps 1, 2 and 3 are sequentially executed, and a detection then proceeds to that at point 4.

At point 4, the previous point in the memory and the present point in the memory are both at the logical high level. In consequence, the detection at the point 4 is completed in a state where counting is not permitted.

In a case where the detection to be made on the state shown in FIG. 11 is started under the condition that counting is permitted, at point 2, the previous point of the present data, the present point of the present data, and the previous point in the memory are all at the logical low level. In consequence, in the detection made at point 2, the processings in steps 1, 8, 9 and 11 are sequentially processed, and a detection then goes to that at point 3.

In the detection made at point 3, since the previous point of the present data, the present point of the present data, and the previous point in the memory are all at the logical low level, the processings in steps 1, 8, 9 and 11 are sequentially processed, and a detection then goes to that at point 4.

At point 4, the previous point of the present data is at the logical low level, and the present point of the present data is at the logical high level. In consequence, in the detection made at point 4, the processing proceeds from step 8, step 9 and then step 10. In step 10, counting permission is cleared, and a detection then goes to that at point 5.

Thus, in the state shown in FIG. 11, whether the detection is started under the condition that counting is permitted or not permitted, counting permission is cleared when the detection at point 5 is to be made.

At point 5, the previous point in the memory and the present point in the memory are both at the logical high level. In consequence, in the detection made at point 5, the processings in steps 1, 2 and 6 are sequentially executed.

At point 6, the previous point in the memory is at the logical high level, and the present point in the memory is at the logical low level. In consequence, in the detection made at point 6, the processings in steps 1, 2, 6, and 7 are successively executed. In step 7, counting is permitted, and a detection then goes to that at point 7.

At point 7, the previous point of the present data is at the logical high level. In consequence, the detection at point 7 is completed after the processings in steps 1 and 8 have been executed.

Thus, in the detection made on the state shown in FIG. 11, no counting is done, and the detection is completed in a state where counting is permitted.

Next, a state shown in FIG. 12 will be described.

In this state, detection may be started under the condition that counting is permitted or not permitted.

First, a case in which counting is not permitted will be described below. At points 2 and 3, the previous point in the memory and the previous point of the present data are both at the logical low level. In consequence, in the detection made at points 2 and 3, the processings in steps 1, 2 and 3 are sequentially executed. Thereafter, a detection goes to that at point 4.

Figure 12:
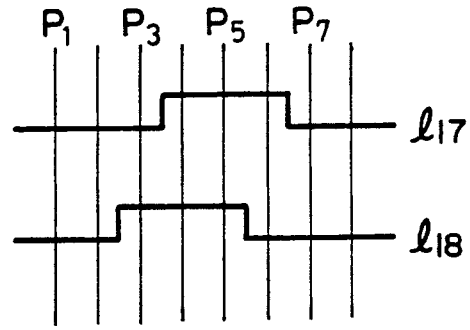

In a case where detection on the state shown in FIG. 12 is started under the condition that counting is permitted, at point 2, the previous point of the present data, the present point of the present data, and the previous point in the memory are all at the logical low level. In consequence, in the detection made at point 2, the processings in steps 1, 8, 9 and 11 are sequentially executed.

In the detection made at point 3, since the previous point of the present data is at the logical low level while the present point of the present data is at the logical high level, the processings in steps 1, 8, 9 and 11 are sequentially executed, and a detection then proceeds to that at point 4 in a state where the counting permission is cleared.

Thus, in the detection made on the state shown in FIG. 12, whether the detection is started under the condition that counting is permitted or not permitted, counting permission is cleared when the detection at point 4 is to be started, and the detection is started at subsequent points in the state where counting is not permitted.

At points 5 and 6, the previous point in the memory and the present point in the memory are both at the logical high level. In consequence, in the detection made at points 5 and 6, the processings in steps 1, 2 and 6 are sequentially executed, and a detection then goes to that at point 7.

At point 7, the previous point in the memory is at the logical high level while the present point in the memory is at the logical low level. In consequence, in the detection made at point 7, the processings in steps 1, 2, 6 and 7 are sequentially executed, and the detection is thereby completed in a state where counting is permitted.

More specifically, in the detection made on the state shown in FIG. 12, no counting is done and the detection is completed in a state where counting is permitted.

Thus, in the detection made on the various patterns shown in FIGS. 5 to 12 in accordance with the flowchart shown in FIG. 4, counting is done only in a state shown in any of FIGS. 8, 9 and 10 where the present data is all at the logical low level while the corresponding data in the memory is at the logical low, high, and then low levels.

In other words, in the present invention, one colony 40 is counted in the state represented by the relationship between the line 6 and line 7 in FIG. 3 in which the present data is all at the logical low level while the data in the memory is at the logical low, high, and then low levels. That is, the number of colonies 40 is incremented by one at the end of that colony 40.

In consequence, in the present invention, the presence of a colony 40 can be detected at the end of that colony 40 by moving the reading unit 10 with the visual sensors 11 incorporated therein along lines selected at an appropriate pitch and by reading data on the individual points set along each line at the same pitch as that of the visual sensors 11 as logical high or low signals.

The values obtained in the above-described counting operation are added and stored in the addition/storage means 24 in the CPU 20, and the results of addition which are stored in the addition/storage means are output to the suitable display 30 by the outputting means 25 when the counting operation is completed.

More specifically, in the present invention, the data on the individual points set on each line is read by the reading unit 10 with the visual sensors 11 incorporated therein as logical high or low signals. The results of the reading performed at the individual points are stored in the storage means 21 until after the data on a subsequent point located on the subsequent line has been read. In consequence, a storage capacity corresponding to one line is sufficient to be used to detect colonies 40.

Figure 13:
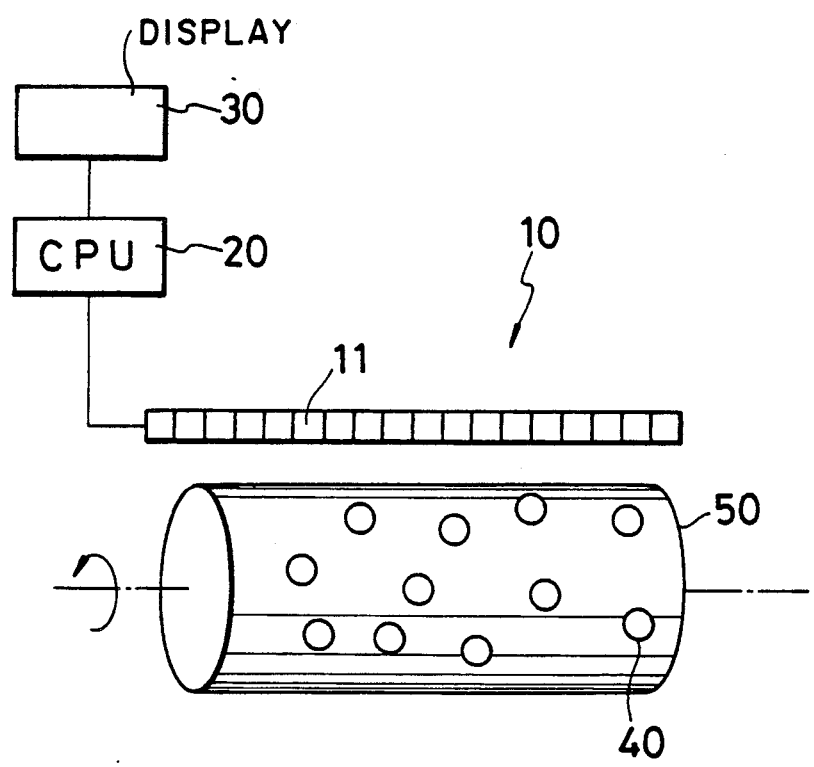
FIG. 13 is a schematic view of another embodiment of the present invention.

FIG. 13 shows another embodiment of the present invention which employs a cylindrical Schale 50. In this case, the Schale 50 is rotated while the reading unit 10 is being fixed during the colony counting operation, which is performed in the same manner as that in which it is performed in the first embodiment.

As will be understood from the foregoing description, in the present invention, the colony number counting operation is performed along the scanning lines. A colony can be detected by comparing the data which is being read with the stored data on the points located between the corresponding portion on a previous scanning line and previous point on the present line. In consequence, the overall storage capacity can be reduced, and the overall size of the apparatus can be thereby made small.

What is claimed is:

1. A colony counting apparatus, comprising:
   a reading unit with a visual sensor incorporated therein, said visual sensor reading data at individual points provided in a line direction as logical high or lower signals;
   a point storage means for storing results of reading, performed by said reading unit, until reading is performed on a subsequent point on a subsequent line;
   a point comparison means for determining when colony counting is permitted, for determining when a colony count value is output after colony counting permitted and for determining when colony counting permission is cancelled by comparing a) data representing a previous point and a present point on a present line from said reading unit with b) data representing a previous point and a present point on a previous line stored in said point storage means,
   wherein said point comparison means determining colony counting permitted when 1) said previous point of the previous line from said point storage means and said previous point of the present line from said reading unit are at said logical high and 2) said present point of the previous line from said point storage means and said present point of the present line from said reading unit are at said logical low,
   wherein said point comparison means determining said colony count value is to be outputted after colony counting permitted when 3) said previous point of the previous line from said point storage means is at said logical high and 4) said present point of the previous line from said point storage means and said previous and present points of the present line from said reading unit are at said logical low, and
   wherein said point comparison means determining colony counting permission cancelled when 5) said previous point of the present line from said reading unit is at the logical low and c) said present point of the present line from said reading unit is at said logical high;
   rewriting means for erasing said data representing a previous point on the previous line after the comparison has been performed by said point comparison means and for string said data from said reading unit on said present point on the present line in said point storage means;
   an addition/storage means for adding and storing said colony count value output from said comparison means; and
   an output means for outputting results of an addition performed by said addition/storage means.

2. A colony counting apparatus according to claim 1, wherein results of the addition are output by an output signal of the output means.

* * * * *